United States Patent
Narayan et al.

(10) Patent No.: US 7,366,934 B1
(45) Date of Patent: Apr. 29, 2008

(54) METHOD OF REMOTELY CONTROLLING DEVICES FOR ENDOSCOPY

(75) Inventors: Anand Narayan, Milpitas, CA (US); Salmaan Hameed, San Jose, CA (US); Kiran A. Javadekar, San Jose, CA (US)

(73) Assignee: Stryker Corporation, Kalamazoo, MI (US)

( * ) Notice: Subject to any disclaimer, the term of this patent is extended or adjusted under 35 U.S.C. 154(b) by 421 days.

(21) Appl. No.: 10/937,850

(22) Filed: Sep. 8, 2004

(51) Int. Cl.
*G06F 1/04* (2006.01)
(52) U.S. Cl. ............... 713/375; 713/300; 713/400
(58) Field of Classification Search ........... 713/300, 713/500, 375, 400
See application file for complete search history.

(56) References Cited

U.S. PATENT DOCUMENTS

| | | | |
|---|---|---|---|
| 5,226,120 A * | 7/1993 | Brown et al. ............ | 709/224 |
| 5,559,496 A * | 9/1996 | Dubats ................. | 340/539.26 |
| 2002/0100054 A1* | 7/2002 | Feinberg et al. ......... | 725/107 |
| 2003/0085814 A1* | 5/2003 | Griep .................. | 340/825.72 |
| 2005/0010861 A1* | 1/2005 | Augustyn et al. ........ | 715/503 |
| 2005/0162282 A1* | 7/2005 | Dresti et al. ........... | 340/825.72 |

OTHER PUBLICATIONS

Tatung Co., "Tatung WebPad-The Wireless Application Enabler", System Specification, http://www.tatungwebpad.com/htm/product_content.htm, Copyright 2002, Printed Aug. 31, 2004, pp. 5 total.

* cited by examiner

*Primary Examiner*—Thomas Lee
*Assistant Examiner*—Malcolm D Cribbs
(74) *Attorney, Agent, or Firm*—Blakely, Sokoloff, Taylor & Zafman LLP

(57) ABSTRACT

A method for remote control of devices. A remote control device receives a graphical user interface from a controlled device. The graphical user interface is periodically updated with controlled device data. The controlled device data is interrupted by command data from the remote control device. The controlled device responds to the command data and updates the graphical user interface.

22 Claims, 12 Drawing Sheets

METHOD OF REMOTELY CONTROLLING DEVICES FOR ENDOSCOPY

TECHNICAL FIELD

At least one aspect of the present invention pertains to the remote control of devices and, more particularly, to a user interface for device control.

BACKGROUND

Endoscopy is a medical field in which internal features of the body of a patient are viewed without the use of traditional, fully-invasive surgery. Endoscopy is now widely used to perform minimally-invasive surgical procedures, such as arthroscopy and laparoscopy. A basic endoscopy tool is the endoscopic camera system. An endoscopic camera system generally includes a scope that is inserted into the body of a patient, a camera that is optically and physically coupled to the scope, and a high intensity light source that is normally coupled to the scope by a fiber optic cable to introduce light into the body. Images acquired by the camera are typically displayed on a conventional video monitor.

The camera is normally coupled through a flexible transmission line to a camera control unit (CCU), which in turn is coupled to a base unit. The CCU processes video data provided by the camera head to generate images, which are coupled through the base unit and displayed on a video monitor. The camera control unit may also be coupled to various multimedia and surgical devices. Multimedia devices may include a printer, a video cassette recorder (VCR) and an image capture device (ICD). Surgical devices may include, for example, insufflators and arthro-pumps, or other devices. Each of these devices must be monitored and controlled during a surgical procedure.

FIG. 1 illustrates a conventional endoscopic control system 100. The base unit 101 is coupled to CCU 102, light source 103, printer 104, VCR 105, ICD 106, arthro-pump 107 and insufflator 108. Status information from each device is coupled to the base unit where it is overlaid on the video image from the CCU and displayed on the video monitor 109. The base unit 101 may have control panel 110 for local control of devices 102-108. Some device functions are also controlled by voice commands using a voice-responsive control system (VCS) 111, which is part of the base unit as shown in FIG. 1. Voice commands are input into a microphone headset 112 worn by the surgeon and coupled to the VCS 111. The VCS employs speech-recognition techniques to generate control signals in response to the voice commands. A handheld control device 113 is cabled to the base unit as an alternative means for controlling devices. The control device is normally used by a nurse to assist the surgeon during operations.

This conventional system configuration has several shortcomings. Because the handheld control device is tethered to the base unit, the mobility of the nurse in the operating room is reduced. Also, the handheld control device has a fixed configuration and cannot be used with more than one base unit, so if it fails the entire system will become unusable. Also, if any problems occur with the operation of the system, it has to be taken out of service for problem diagnosis and repair.

SUMMARY OF AN EMBODIMENT OF THE INVENTION

One aspect of the present invention is a method for transferring a graphical user interface from a base unit to a remote control unit. The remote control unit issues periodic service requests to the base unit. The remote control unit receives device data from the base unit in response to the periodic service requests and the graphical user interface is updated with the device data. The remote control unit interrupts the device data in response to user initiated service requests. Other aspects of the invention include an apparatus and a system which can perform such a method.

Other features of the present invention will be apparent from the accompanying drawings and from the detailed description which follows.

BRIEF DESCRIPTION OF THE DRAWINGS

One or more embodiments of the present invention are illustrated by way of example and not limitation in the figures of the accompanying drawings, in which like references indicate similar elements and in which.

DETAILED DESCRIPTION

Figure 1:
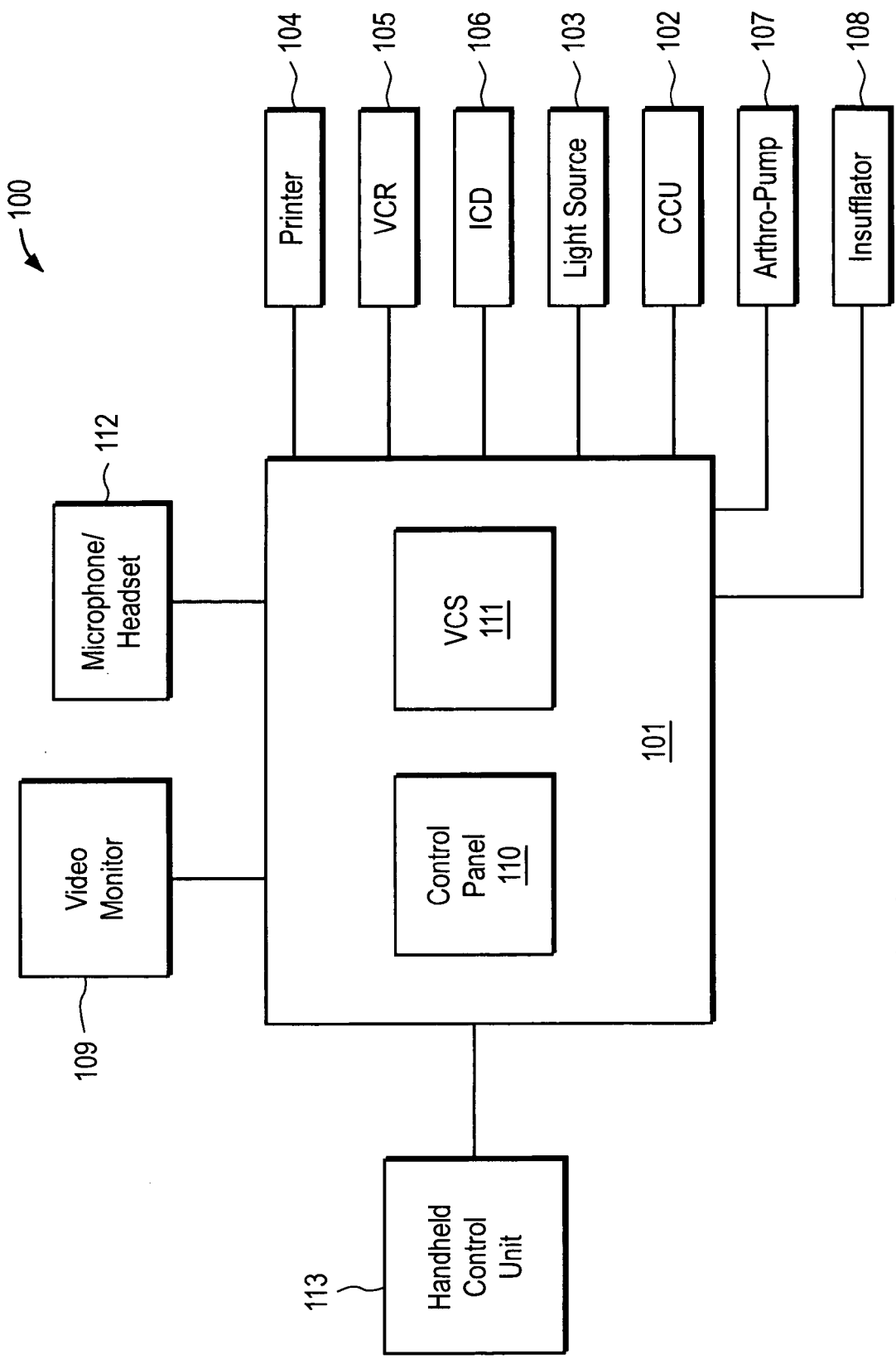
FIG. 1 illustrates a conventional endoscopic control system.

In the following description, numerous specific details are set forth such as examples of specific systems, languages, components, etc. in order to provide a thorough understanding of the present invention. It will be apparent, however, to one skilled in the art that these specific details need not be employed to practice the present invention. In other instances, well-known materials or methods have not been described in detail in order to avoid unnecessarily obscuring the present invention.

The present invention includes operations, which will be described below. The operations of the present invention may be embodied in machine-executable instructions, which may be used to cause a general-purpose or special-purpose processor programmed with the instructions to perform the operations. Alternatively, the operations maybe performed by a combination of hardware and software.

The present invention may be provided, at least in part, as a computer program product, or software, that may include a machine-readable medium having stored thereon instructions, which may be used to program a computer system (or other electronic devices) to perform a process according to the present invention. A machine-readable medium includes any mechanism for storing or transmitting information in a form (e.g., software, processing application) readable by a machine (e.g., a computer). The machine readable medium may include, but is not limited to: magnetic storage media (e.g., floppy diskette); optical storage media (e.g., CD-ROM); magneto-optical storage media; read only memory (ROM); random access memory (RAM); erasable programmable memory (e.g., EPROM and EEPROM); flash memory; electrical, optical, acoustical or other form of propagated signal; (e.g., carrier waves, infrared signals, digital signals, etc.); or other type of medium suitable for storing electronic instructions.

The present invention may also be practiced in distributed computing environments where the machine-readable medium is stored on and/or executed by more than one computer system. In addition, the information transferred between computer systems may either be pulled or pushed across the communication medium connecting the computer systems.

Some portions of the description that follow are presented in terms of algorithms and symbolic representations of operations on data bits that may be stored within a memory and operated on by a processor. These algorithmic descriptions and representations are the means used by those skilled in the art to effectively convey their work. An algorithm is generally conceived to be a self-consistent sequence of acts leading to a desired result. The acts are those requiring manipulation of quantities. Usually, though not necessarily, these quantities take the form of electrical or magnetic signals capable of being stored, transferred, combined, compared and otherwise manipulated.

A system for the remote control of devices is described. In one embodiment, and as described in greater detail below, the system includes a base unit having a wireless interface, slave devices connected to the base unit, and a wireless control unit (WCU). The base unit controls the slave units in response to commands from the WCU. The base unit also receives device status information from the slave devices, which it sends to the WCU in response to requests from the WCU. The base unit, the slave devices and the WCU form at least part of a network on which each has an assigned address to facilitate the routing of data and commands. The WCU runs a graphical user interface (GUI) application, which the WCU can download from the base unit or another location on the network. The GUI displays icons for the slave devices that are connected to the base unit, and dynamically changes the displayed icons when the configuration of slave devices changes. The icons may appear as soft-keys on a touch-screen. The WCU may also download a library of display screens from the base unit, or the network, corresponding to each of the possible slave units that might be connected to the base unit. When a user of the WCU selects the icon of a particular device that is displayed on the GUI, the screen for that slave device is displayed on the WCU. The screen for the selected slave device is populated with soft-keys customized to control that particular slave device, as well as active display areas which provide device status information to the user of the WCU. The WCU periodically polls the base unit for device status changes to insure that the user is provided with current data. Because the generic GUI and the library of device screens are resident in the wireless control device, the communication link between the WCU and the base unit is only required to transmit changes to the GUI and the device screens, and the link is not burdened with a continuous overhead of graphics data transmission.

Figure 2:
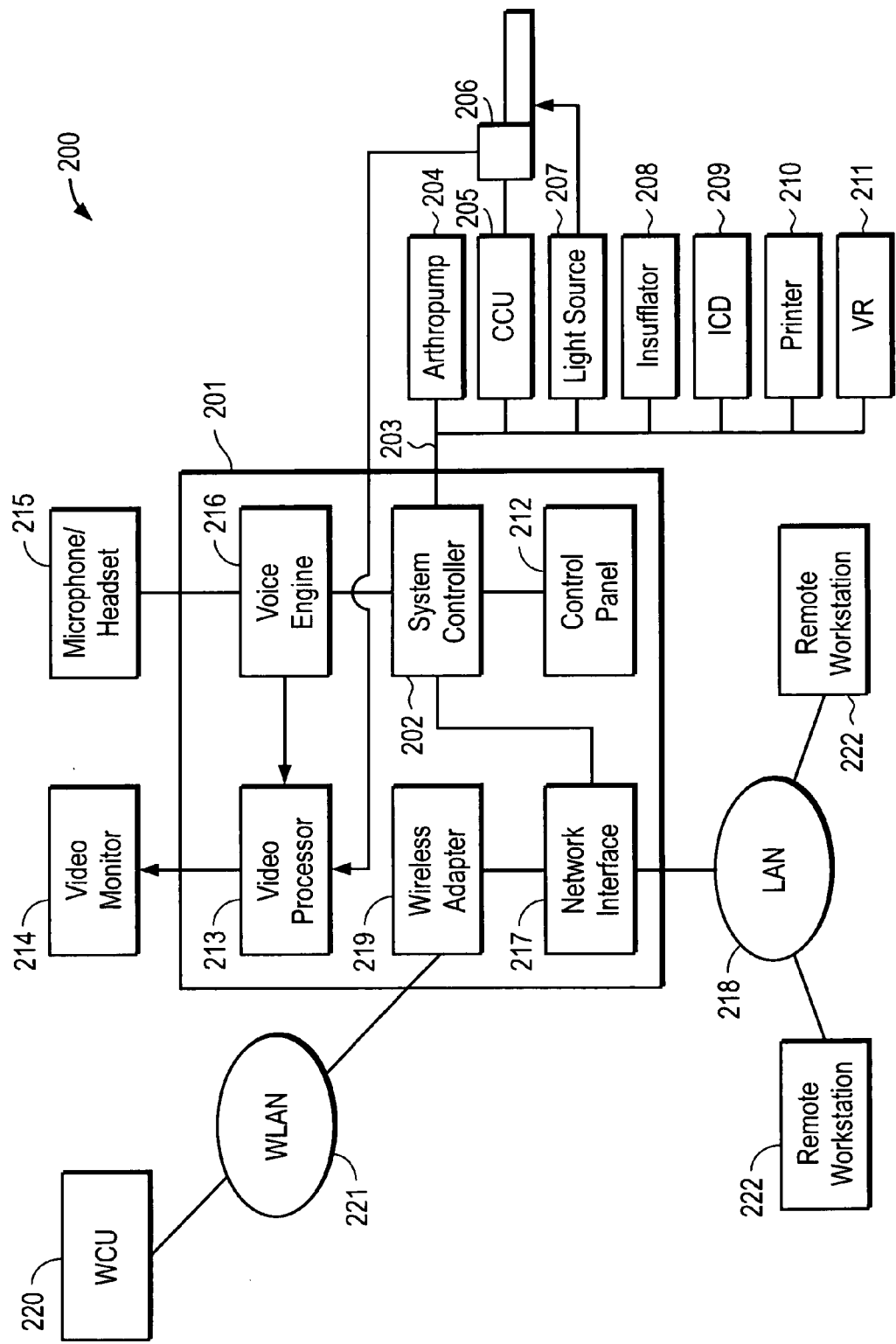
FIG. 2 illustrates an endoscopic control system in one embodiment of wireless control of devices for endoscopy.

FIG. 2 illustrates a system 200 in one embodiment of remote control of devices. System 200 may include a base unit 201. Base unit 201 may include system processor 202 which may be connected to slave devices on a bus 203 which may be a serial bus. Slave devices may include arthro-pump 204, camera control unit (CCU) 205, endoscopic camera 206, light source 207, insufflator 208, image capture device (ICD) 209, printer 210 and video recorder (VR) 211. System processor 202 may be connected to control panel 212, which may an LCD touch-screen control panel that provides local control of the slave devices that are connected to system processor 202. Video images from camera 206 are processed by video processor 213 for display on video monitor 214. The video images may be overlaid with data and graphics pertaining to the status of slave devices 204-211 in response to voice commands issued at microphone headset 215 and processed through voice engine 216. System processor 202 may receive device control commands from voice engine 216 in response to voice commands entered at microphone headset 215. System processor 202 may also be connected to network interface 217 which may in turn be connected to local area network (LAN) 218. LAN 218 may be, for example, a wired Ethernet LAN, a wireless LAN such as an 802.11b LAN, a Bluetooth LAN, etc. LAN 218 may provide access to remote workstations 222. The remote workstations 222 may be conventional computer workstations as are known in the art, which may be capable of executing a web browser program such as Microsoft Internet Explorer or Netscape Navigator. System processor 202 may also be connected to wireless adapter 219. The wireless adapter 219 may be, for example, a conventional wireless adapter such as an 802.11b wireless Ethernet adapter, a Bluetooth adapter, etc. Wireless adapter 219 may provide a communication link to wireless control unit (WCU) 220 through wireless LAN (WLAN) 221.

Figure 3:
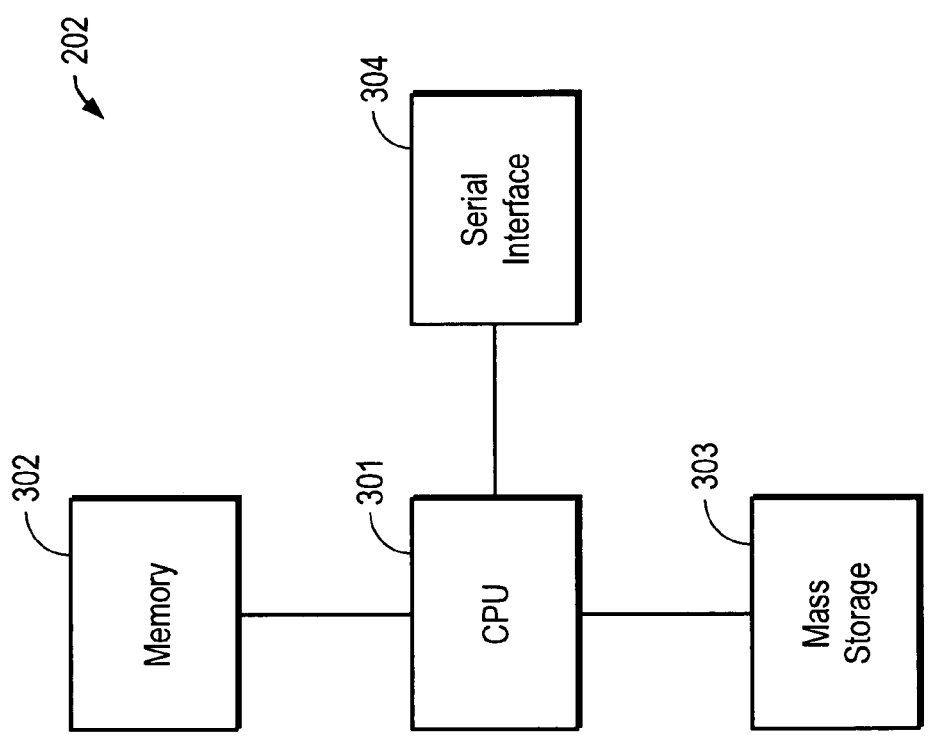
FIG. 3 illustrates a system processor in an embodiment of remote control of devices.

FIG. 3 illustrates a block diagram of system processor 202, at least in one embodiment. As shown, system processor 202 includes a central processing unit 301. Also included in the system processor 202, and coupled to the CPU 301 are a system memory 302, a mass storage device 303, and a serial interface 304. System memory 302 is used for storage of software instructions and related data. System memory may include volatile memory, non-volatile memory or both. Any such volatile memory may be, for example, any type of random access memory (RAM) such as static RAM (SRAM) or dynamic RAM (DRAM). Any such non-volatile memory may be, for example, any type of read only memory (ROM) such as electronically programmable ROM (EPROM) or flash memory, etc. Mass storage device 303 may be used for permanent storage of programs and data and may be any type of non-volatile storage medium such as a magnetic hard drive, floppy disk, a read-write CD-ROM or DVD, etc. Serial interface 304 may be used to interface with and control slave devices such as slave devices 204-211. Serial interface 304 may be a universal serial interface which may be compatible with EIA (Electronic Industries Association) serial interface standard 232, IEEE (Institute of Electrical and Electronic Engineers) serial interface standard 1394, or USB (Universal Serial Bus) standards. System processor 202 may also be connected to a system bus (not shown), such as a PCI bus, to communicate with other components of the base unit 201.

Figure 4:
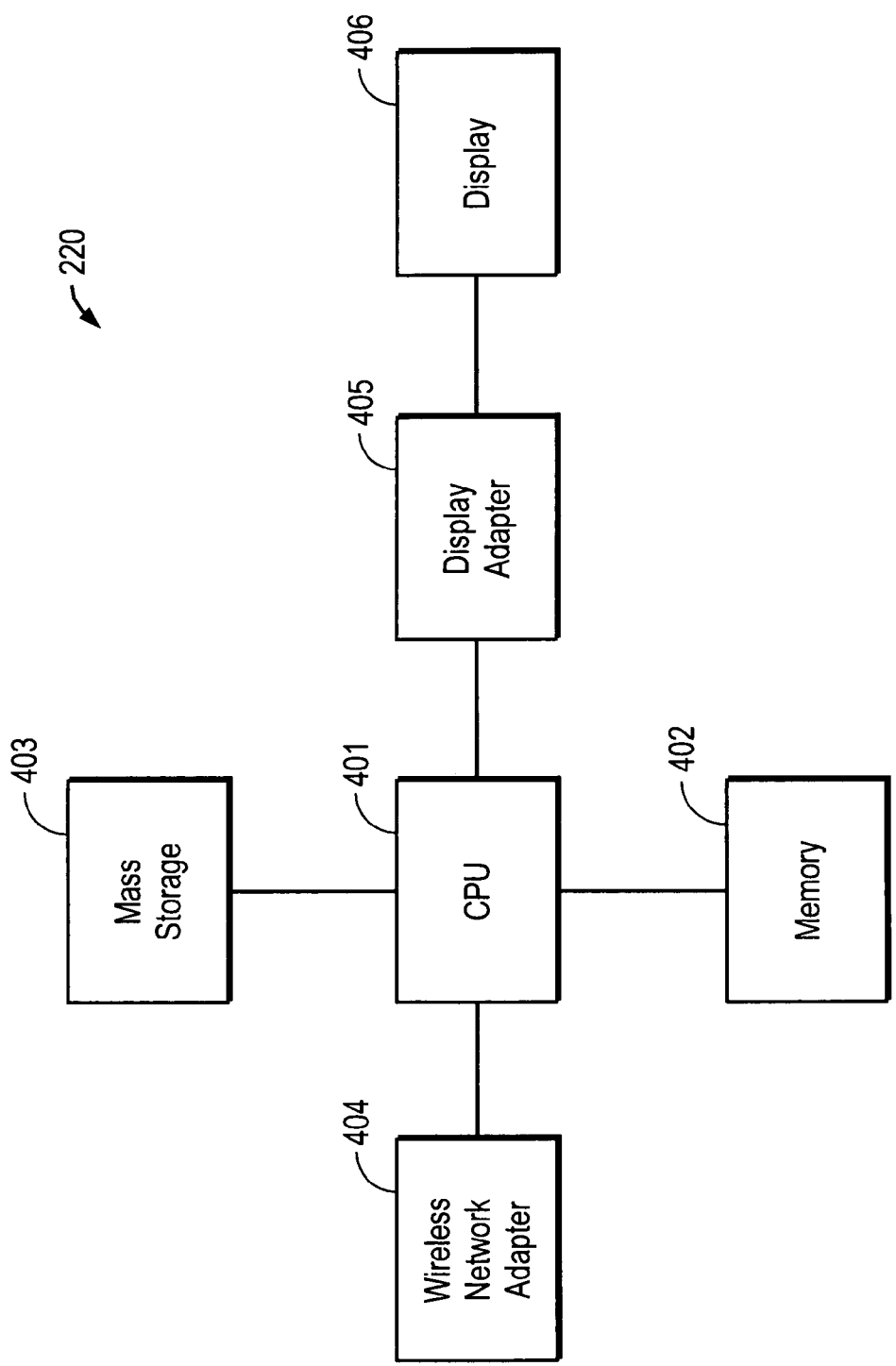
FIG. 4 illustrates a wireless control unit in another embodiment of remote control of devices.

FIG. 4 illustrates a wireless control unit (WCU) 220 in one embodiment. As shown, WCU 220 includes a central processing unit 401. Also included in the WCU 220, and coupled to the CPU 401 are a system memory 402, a mass storage device 403, a wireless network adapter 404 and a display adapter 405. System memory 402 is used for storage of software instructions and related data. System memory may include volatile memory, non-volatile memory or both. Any such volatile memory may be, for example, any type of random access memory (RAM) such as static RAM (SRAM) or dynamic RAM (DRAM). Any such non-volatile memory may be, for example, any type of read only memory (ROM) such as electronically programmable ROM (EPROM) or flash memory, etc. Mass storage device 403 may be used for permanent storage of programs and data and may be any type of non-volatile storage medium such as a magnetic hard drive, floppy disk, flash memory, etc. Wireless network adapter 404 may be, for example, a conventional wireless adapter such as an 802.11b wireless Ethernet adapter, a Bluetooth adapter, or similar wireless adapter. Wireless network adapter 404 may provide a communication link to base unit 201 through wireless LAN (WLAN) 221. Display adapter 405 interfaces the CPU 401 with display 406. Display 406 may be an LCD touch-screen display. Accordingly, display adapter 405 may include touch-screen sensors (not shown).

Some features of the system processor 202 and the WCU 220 may be implemented in software, at least in part. The software may be executed as appropriate by CPU 301 and CPU 401 or by other components such as serial interface 304, wireless adapters 219 and 404, and display adapter 405.

Figure 5:
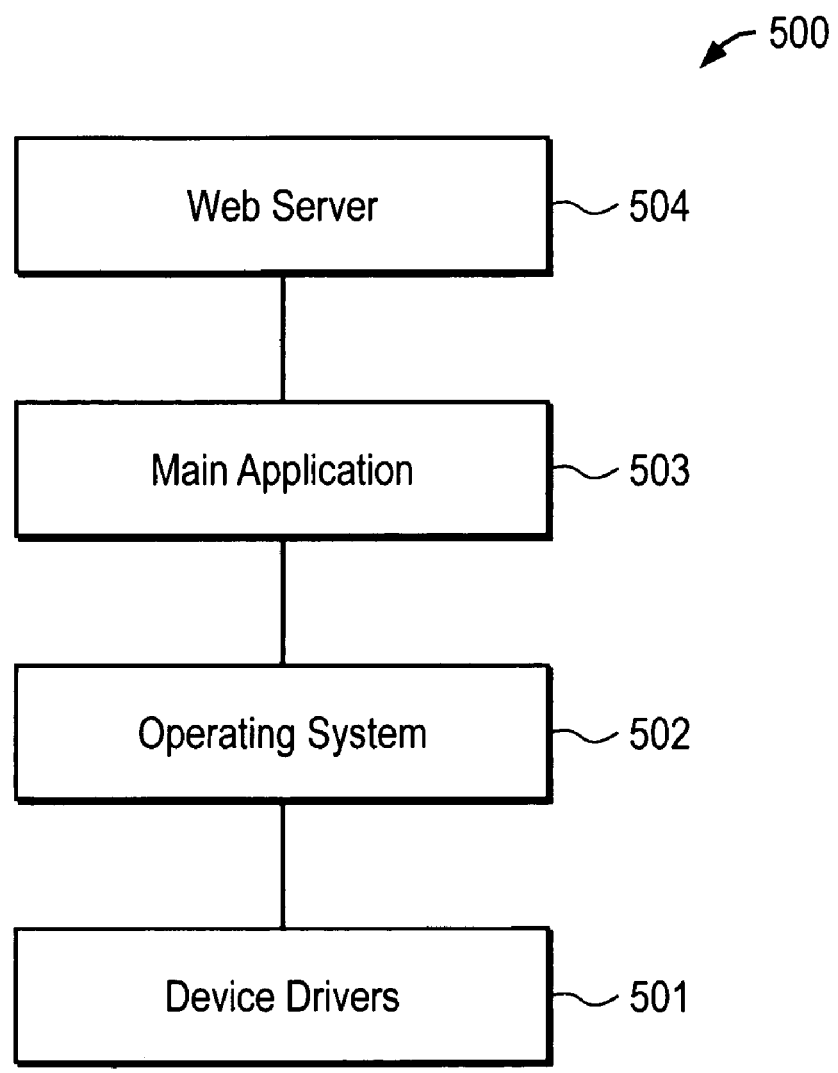
FIG. 5 illustrates a software configuration of a system processor in one embodiment of device control.

FIG. 5 shows the overall software configuration of the system processor 202. As shown in FIG. 5, the software 500 associated with the system processor 202 includes 4 major components: a device driver layer 501, an operating system 502, a main application layer 503 and a web server component 504. The operating system 502 may be a conventional operating system, such as Microsoft Windows 2000, Windows XP or a custom embedded operating system based on Windows XP Embedded. The device driver layer 501 provides an interface between the operating system 502 and the hardware components (see FIG. 3) of the system processor 202. The main application layer 503 runs on top of the operating system and includes a device control manager for control of devices 204-211. The web server 504 is a program that, using the client/server model and the world wide web's hypertext transfer protocol (HTTP), serves the files that form web pages to web users. Examples of such files are hypertext markup language (HTML) files and extensible markup language (XML) files. Client/server describes the relationship between two computer programs in which one program, the client, makes a service request to another program, the server, which fulfills the request. The software 500 in the system processor 202 may be stored at least partially in memory 302 (FIG. 3). The software may also be stored at least partially in mass storage device 303.

Figure 6:
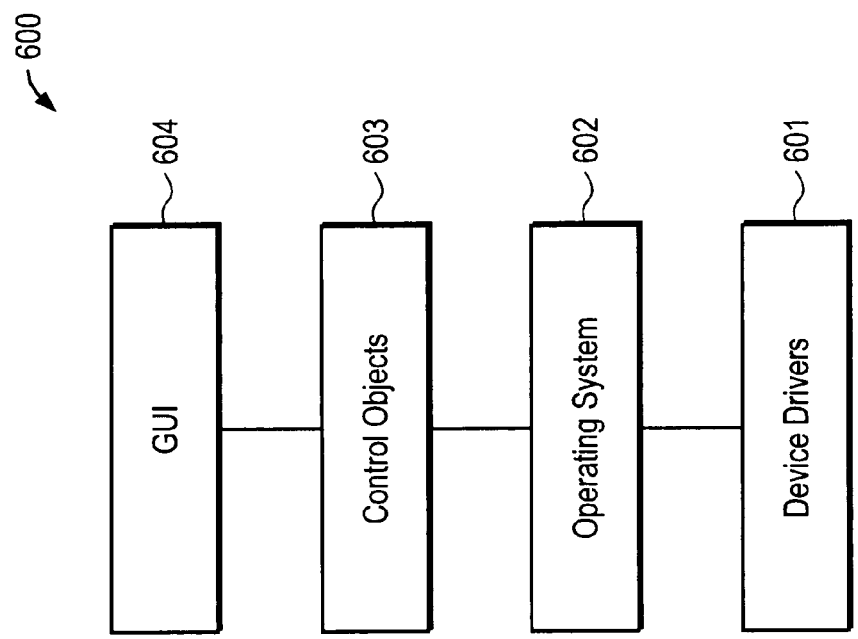
FIG. 6 illustrates a software configuration of a wireless control unit in one embodiment of remote control of devices.

FIG. 6 shows the overall software configuration of the WCU 220. As shown in FIG. 6, the software 600 associated with the WCU 220 also includes four major components: a device driver layer 601, an operating system 602, a control layer 603, and a graphical user interface 604. The operating system 602 may be a conventional handheld device operating system such as Microsoft Windows CE. Device drivers 601 provide an interface between the operating system 602 and the hardware components of the WCU (see FIG. 4). The control layer 603 may contain applications and control objects, which may be Java applications, Java applets, ActiveX controls or similar applications and control objects. Java and ActiveX are known in the art and will not be discussed in detail here. The control layer generates the GUI 604, which provides the high level functions that enable a user to control the base unit 201 through system processor 202. The software 600 in the WCU 220 may be stored at least partially in memory 402 (FIG. 4). The software may also be stored at least partially in mass storage device 403.

Figure 7:
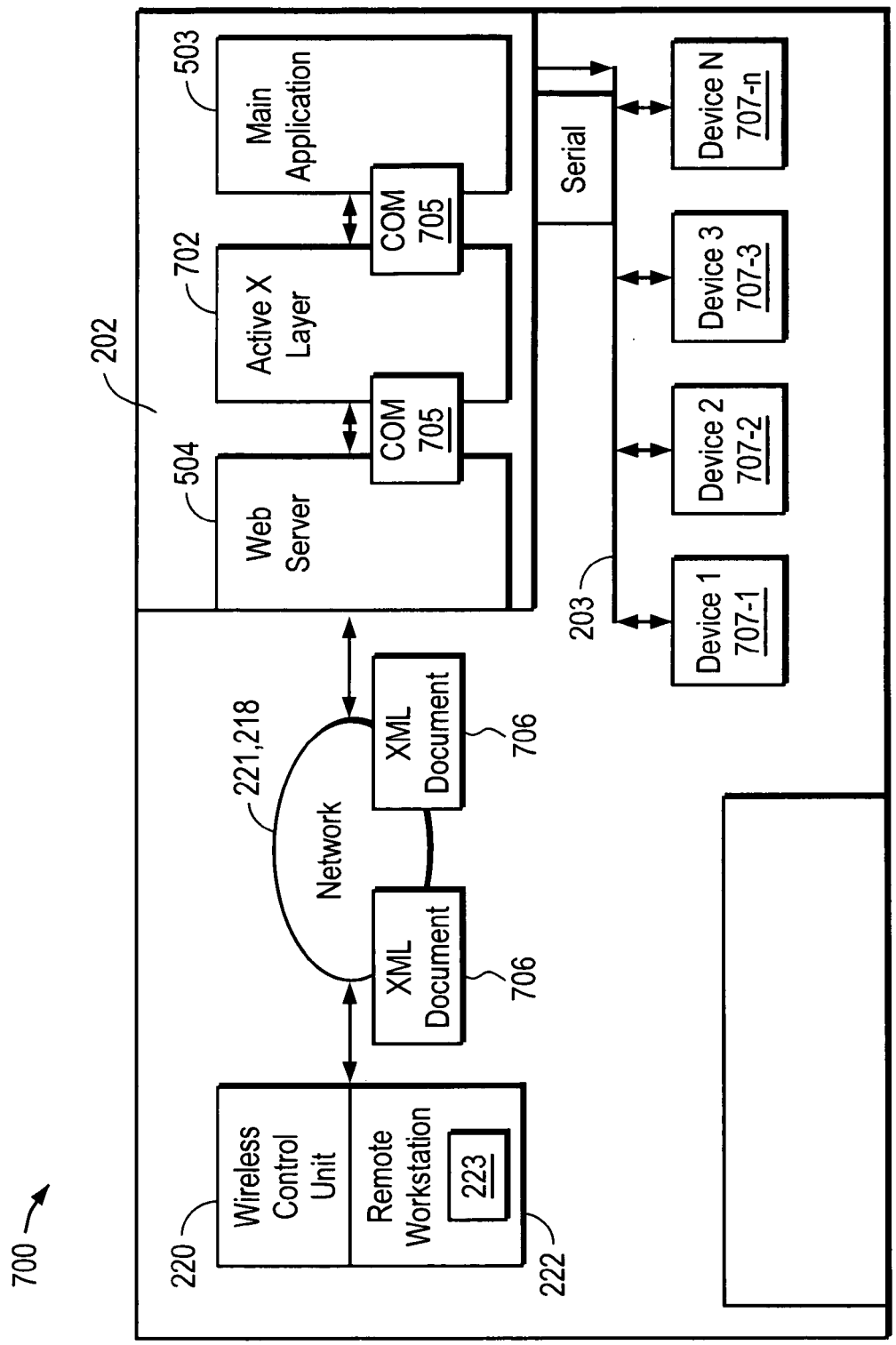
FIG. 7 illustrates a system architecture in one embodiment of a system for the remote control of devices.

FIG. 7 illustrates a system architecture in one embodiment of a system for the remote control of devices. In the exemplary embodiment, system processor 202 may be configured as a server, and WCU 220 and remote workstations 222 may be configured as clients. Main application 503 may send control commands to devices 707-1 through 707-*n* (collectively devices 707) on bus 203. Devices 707 may be any one or more of slave devices 204 through 211 (see FIG. 2). Main application 503 may have an interface to an ActiveX layer 702, to enable a COM (component object module) agent 704 to get and set the status of devices 707. The ActiveX layer 702 may convert low level data coming from the main application 503 into a high level format that may be understood by WCU 220 and remote workstations 222. ActiveX layer 702 may pass the converted data in a COM 705 to web server 504. Web server 504 may utilize active sever pages to determine dynamically at runtime what devices 707 are connected to the base unit 201 and what is the current status of devices 707. Web server 504 may receive COM 705 data, and package COM 705 data into a format that may be transmitted over the WLAN 221 or the LAN 218. The format may be, for example, an XML document 706. The XML document 706 may be transmitted over the network 221 or the network 218, which may be conventional TCP/IP (transmission control protocol/internet protocol) networks using a conventional HTTP protocol. WCU 220 may be executing a Java application in control layer 603 (see FIG. 6) to generate a GUI at the display 406 (see FIG. 4) of WCU 220. Similarly, remote workstation 222 may be executing Java applets within a browser 223. Upon receipt of the XML document 706, the WCU 220 and/or the remote workstations 222 may update their running applications to refresh their displays. It will be appreciated that the foregoing process may be reversed from end-to-end when commands or service requests are issued at the GUI of either the WCU 220 or the remote workstation 222.

Figure 8:
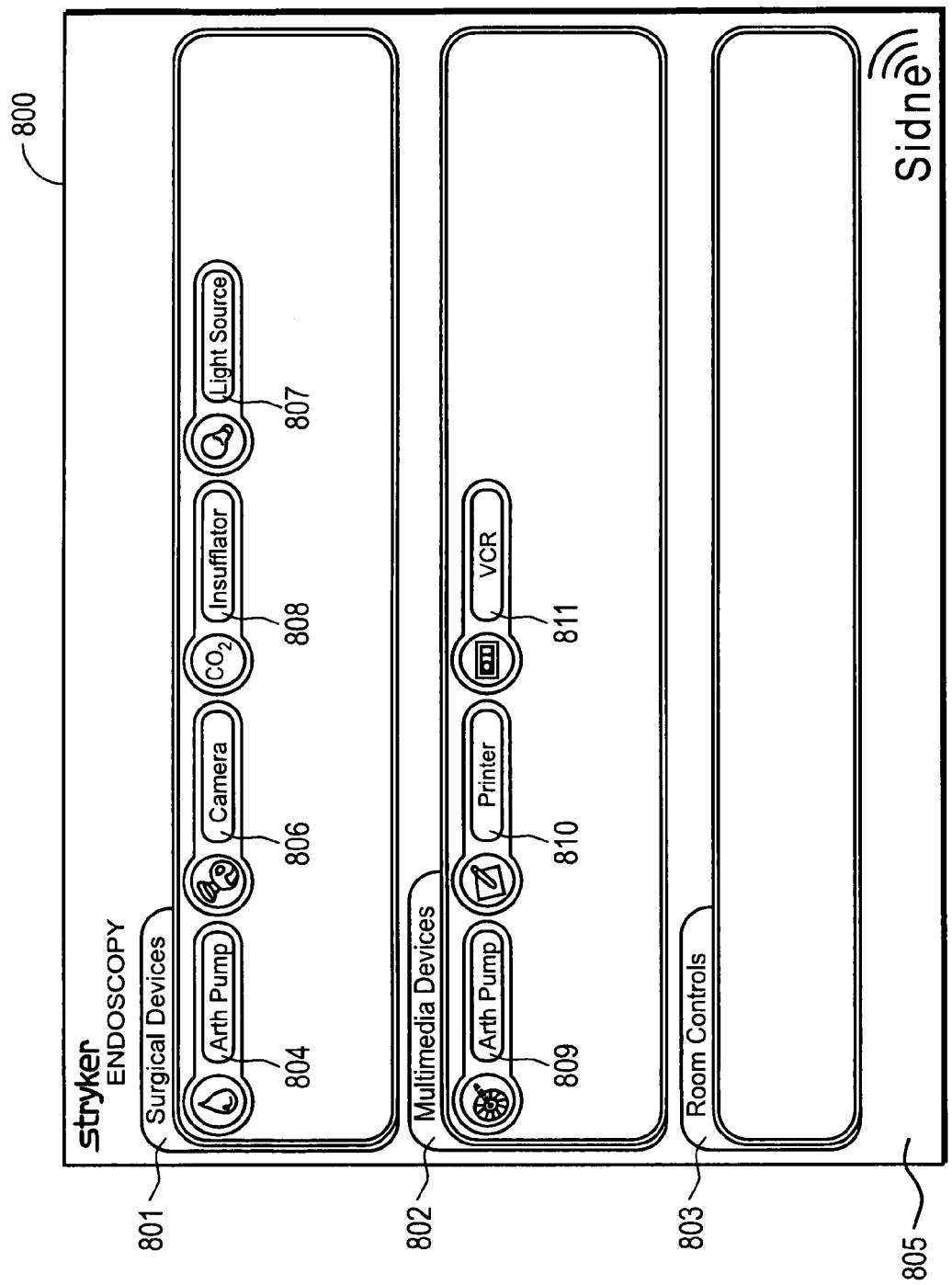
FIG. 8 illustrates a graphical user interface in one embodiment of remote control of devices.

FIG. 8 illustrates a GUI 800 that may be displayed on display 406 of WCU 220. A generic GUI comprising the background areas 801, 802, 803 and 805 may have been downloaded to WCU 220 as part of an initialization and synchronization process, described in greater detail below. Generic GUI 800 may correspond visually to the GUI layer 604 in the software configuration 600 of the WCU 220. At startup, a process in the control layer 603 issues a service request to the system processor 202 querying for current device status, and updates the GUI 800, accordingly, with appropriate icons corresponding to any devices 204-211 (see FIG. 2) which are connected to base unit 201, and active. At the point in time depicted by FIG. 8, for example, the system processor 202 has reported to the WCU 220 that arthropump 204, camera 206, insufflator 208 and light source 207 are surgical devices which are connected to base unit 201. Accordingly, the GUI 800 displays corresponding icons 804, 806, 808 and 807. Similarly, in the example shown in FIG. 8, the base unit has reported that ICD 209, printer 210 and VCR 211 are multimedia devices which are connected to base unit 201. Accordingly, the GUI 800 displays corresponding icons 809, 810 and 811. The process running in the control layer 603 may issue periodic (e.g., at one second intervals) service requests for device status changes in the form of a get_device_status command. If there are no device status changes from the previous status report, the system processor 202 responds with a "no change" message. If there are device status changes, the system processor 202 responds with an "update" message to notify the WCU 220 that a data thread is about to be initiated, whereupon the system processor 202 begins transmitting the data thread to the WCU 220. The base unit continues the data thread until the data thread is completed or the data thread is interrupted by a user initiated service request from the WCU 220, as described below. If a device is unplugged from the base unit 201, the next service request from the WCU 220 will generate a data thread noting the change, and the icon for the device will be removed from the GUI 800. Similarly, if a new device is plugged into the base unit 201, that change will be reported by the system processor 202 in the next data thread, and a corresponding icon for the new device will be displayed.

Figure 9:
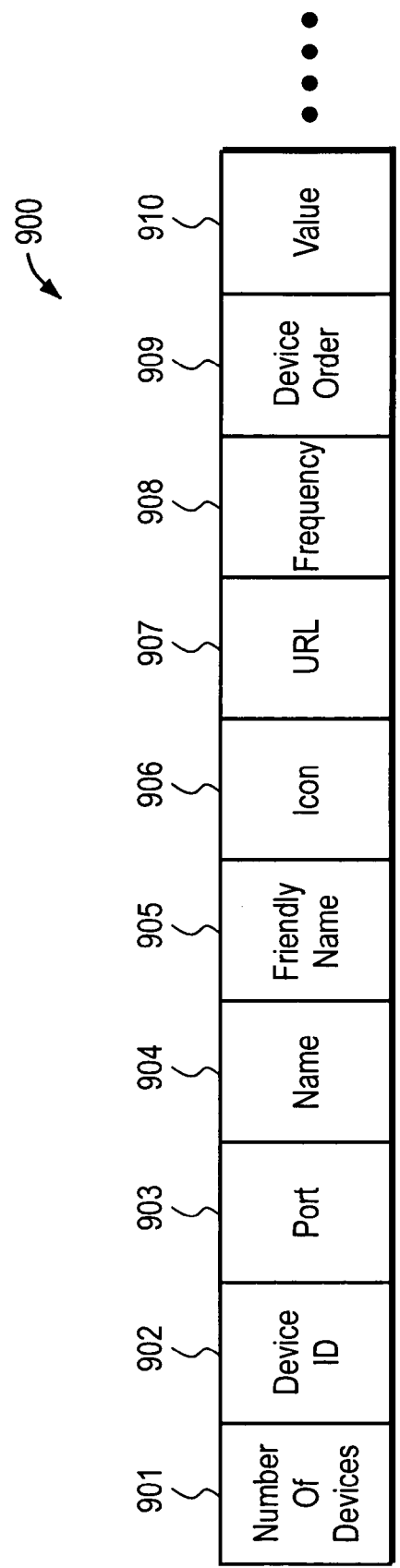
FIG. 9 illustrates a data structure in one embodiment of device control.

The data thread may have a data structure that is understood by the WCU 220. For example, the data thread, which may be in the form of an XML document as previously described, may have a data structure 900 as shown in FIG. 9. The data structure may include the following fields: a 'number_of_devices' field 901 which returns the number of devices currently connected to the base unit 201; a 'device_id' field 902 which contains a unique device identifier; a 'port' field 903 which specifies which port on the base unit 201 the device is connected to; a 'name' field 904 which is an internal name for the device; a 'friendly_name' field 905 which is an external name for the device (e.g., light source); an 'icon' field 906 which contains the URL of the image icon to be displayed for the device; a 'URL' field 907 which contains the URL of the device specific screen for the device; a 'frequency' field 908 which indicates the 'device_order' field 909 which indicates where in the GUI 800 the device icon is to be displayed; and a 'value' field 910 which contains all of the current operating values and or settings for the device. This sequence of fields 902 through 910 is repeated for each device corresponding to the number of devices specified by field 901. Upon connection of a new device to the base unit, the XML document may be updated with a new device structure 900 for the new device and the number_of_devices field value would be increased by 1. Similarly, on disconnection of a device, the device structure for that device would be removed and the number_of_devices field value would be decreased by 1.

Figure 10:
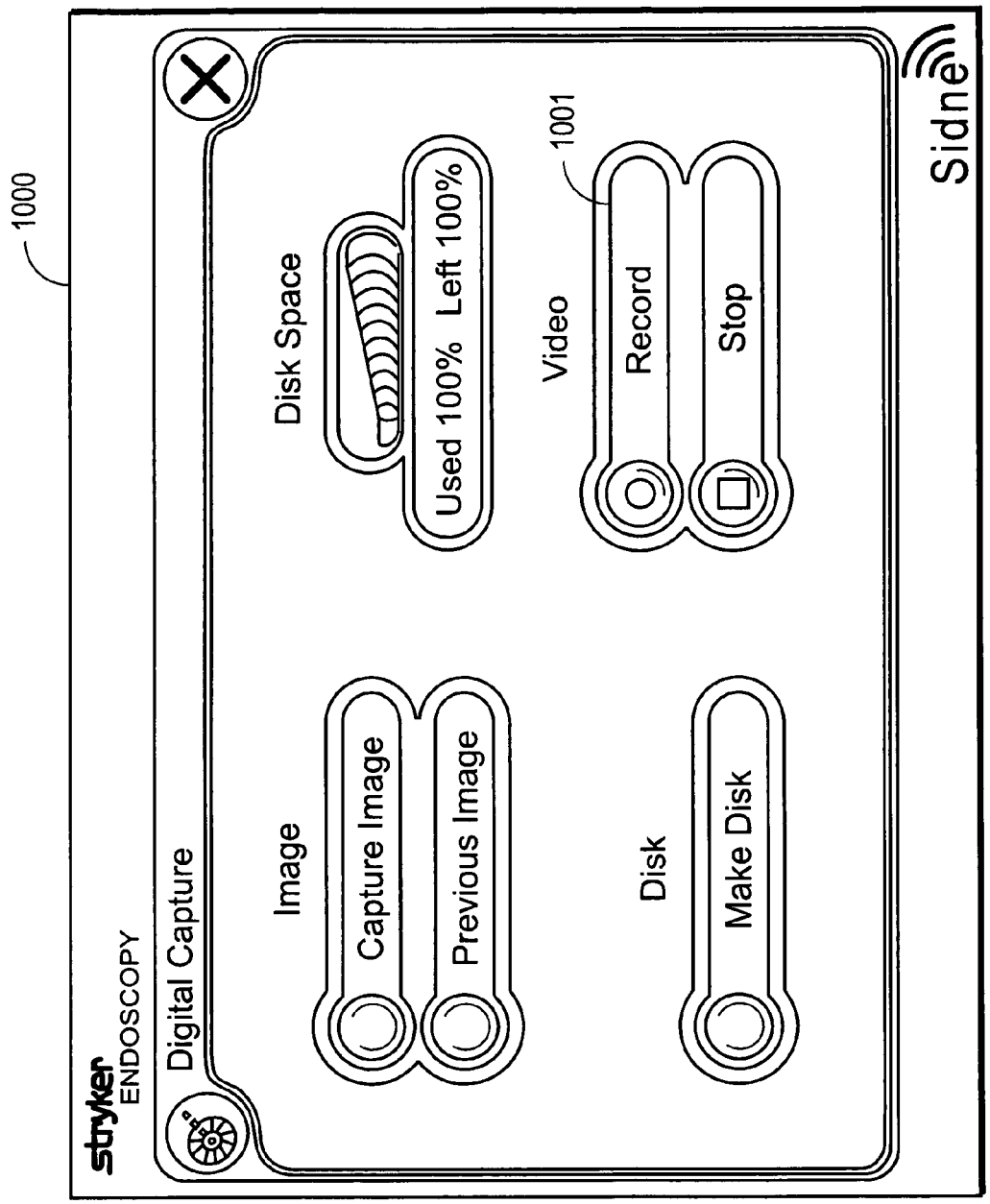
FIG. 10 illustrates another graphical user interface in an embodiment of remote control of devices.

As discussed above, once a data thread such as the data thread 900 has started, the system processor 202 will continue the data thread to its end unless interrupted by a service request from the WCU 220. The user initiated service request functions as a command thread, which always takes priority over the current data thread. That is, the system processor 202 treats any command thread as a priority interrupt, services the command thread, and then continues the interrupted data thread after a programmed delay time. The programmed delay time allows a user to initiate more than one service request before the data thread restarts. For example, if a user touches a device icon, such as Digital Capture icon 809, any in-process data thread will be halted and then restarted with any changes that are responsive to a command associated with the icon 809. In the example given, the command associated with the icon 809 may be a command to display a Digital Capture device screen 1000, as shown in FIG. 10, corresponding to the status of the Digital Capture Device 209. The data thread for the selected device may be updated periodically as described above for the generic GUI 800. The data thread for the device screen may have a data structure similar to the data structure comprising fields 902 through 910 for a single device. The data thread may be continuously updated until the WCU 220 issues another service request, for example, in response to a user action, such as pressing a button on the display 1000.

Because the data thread is always paused by user action, and resumed with any changes that are responsive to the user action, the user receives immediate feedback even if the requested action is not performed. For example, if the user touches record button 1001, the local application running on the WCU 220 will send a command to the system processor 202 to instruct the recorder 209 to begin recording. The system processor will acknowledge the request by sending an updated data thread which causes the WCU 220 to display, for example, a depressed or highlighted record button. If the command is executed properly, the system processor 202 will continue to send "no change" responses to the periodic service requests from the WCU 220 and the GUI will continue to display a depressed or highlighted record button. If the command cannot be executed for any reason, the system processor 202 will respond to the next service request with an "update" message and send a data thread which returns the display to its previous state, indicating that the command was not serviced.

Figure 11:
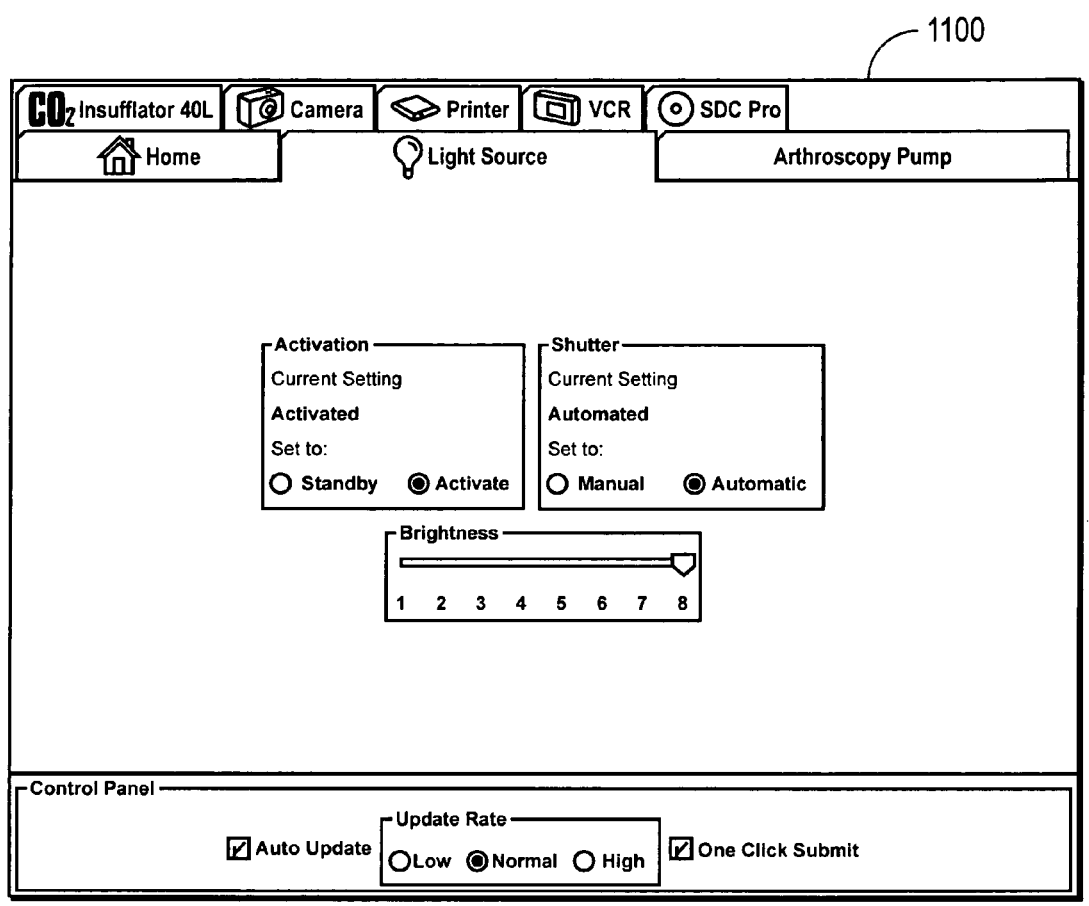
FIG. 11 illustrates a graphical user interface in another embodiment of remote control of devices.

It will be appreciated that the processes described above may be applied equally in the case where the WCU 220 is replaced by one of remote workstations 222, on LAN 221, executing a browser 223. FIG. 11 illustrates, for example, a GUI 1100 that may be executed on remote workstation 222 where GUI 1100 may be configured to respond to mouse and keyboard inputs which are conventionally associated with workstations such as IBM PC's or Apple Macintosh computers. It will also be appreciated that the GUI 1100 may be configured to provide system status information to a user that may be used for system diagnosis, maintenance or repair.

As discussed briefly above, a wireless client device such as WCU 220 may not have had a previous association with a particular base unit such as base unit 201. Alternative, the WCU 220 may have been a client of a different server, associated with a different base unit or a different type of equipment. Therefore, the WCU 220 may have no GUI configuration or a GUI configuration that is not compatible with the configuration of the base unit 201. The WCU 220 may therefore contain a synchronization program to establish an initial secure communication link with the base unit 201, and an auto update application that is the first program that runs after the WCU 220 is synchronized with base unit 201 and is also the first program that runs when the WCU 220 is powered up after previously being synchronized. The synchronization program may be initiated by a user if the WCU 220 does not display the correct GUI for the base unit 201. Alternatively, the WCU 220 may automatically synchronize with base unit 201. After the WCU 220 is synchronized with the base unit 201, the auto update program may query the system processor 202 for a list of the latest versions of all of the files that the WCU 220 will need to create the GUI's that are required to control the base unit 201. The WCU 220 may download the necessary files from the system processor 202. Alternatively, the WCU 220 may be directed to a location on the network 218 where the files are stored, and the WCU 220 may download the necessary files from that location.

Figure 12:
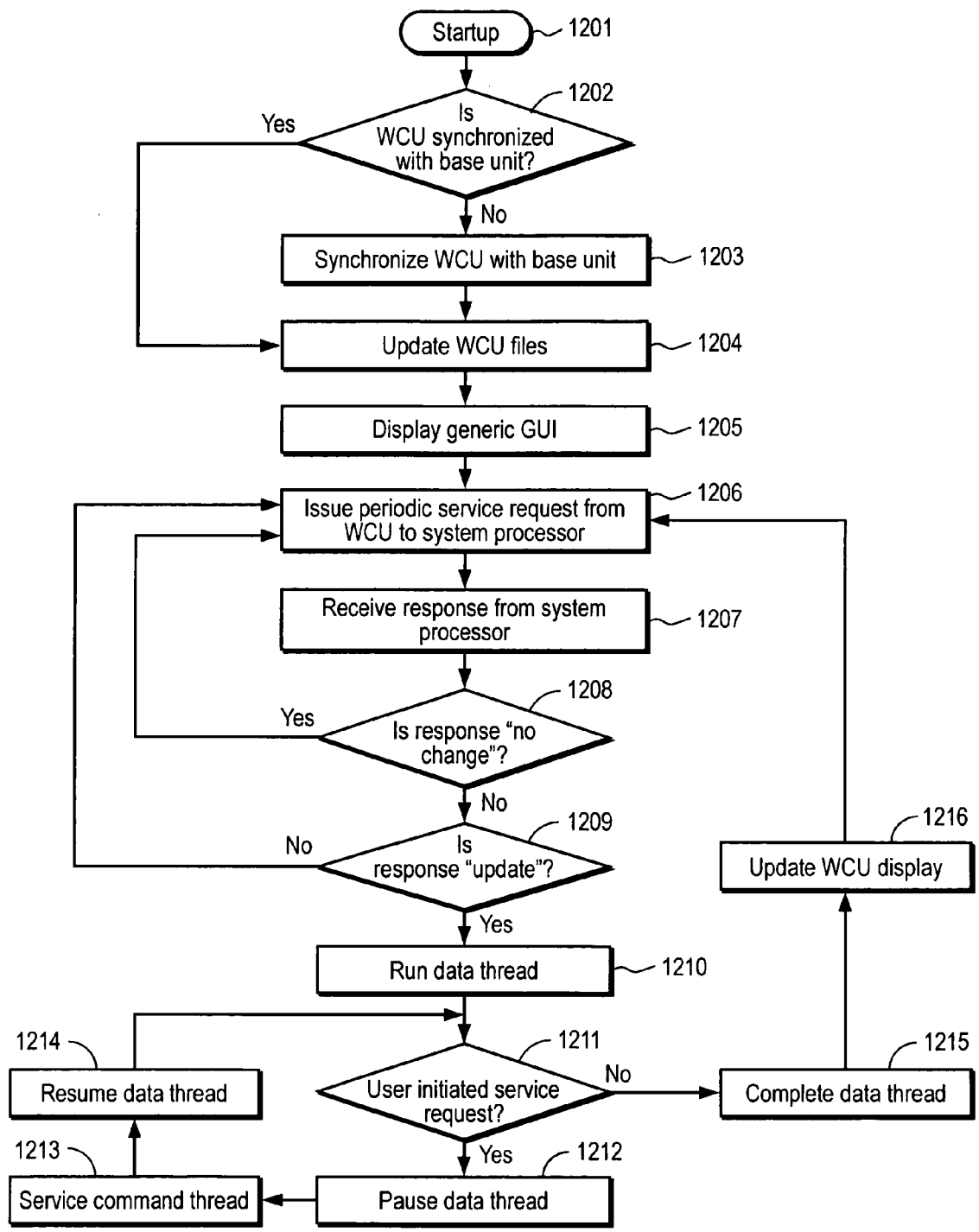
FIG. 12 illustrates one embodiment of a method for remote control of devices.

FIG. 12 illustrates an embodiment of the method described above. The method begins when the WCU 220 is started up, operation 1201. Next, in operation 1202, the WCU 220 determines if it is synchronized with the base unit 201, either automatically or in response to a user action as described above. If the WCU 220 is not synchronized with base unit 201, the WCU 220 synchronizes with the base unit 201 at operation 1203. If the WCU 220 is synchronized with base unit 201, the method continues at operation 1204 where the WCU 220 runs the auto update program to update its files. In operation 1205, the updated files are used to generate and display the generic GUI 800. At operation 1206, the WCU 220 issues a periodic service request and receives a response from system processor 202 at operation 1207. If the response is "no change" at operation 1208, the method returns to operation 1206 where the next periodic service request is issued. If the response is "update" at operation 1209, the system processor 202 runs a data thread 900 at operation 1210. During the transmission of the data thread 900, the system processor 202 monitors the WCU 220 for a user initiated service request, operation 1211. If a user initiated service request is detected at operation 1211, the current data thread 900 is paused at operation 1212. In operation 1213, the command thread generated by the user initiated service request is serviced by the system processor 202. At operation 1214, the data thread 900 is resumed with the changes that are responsive to the command thread and the method resumes at operation 1211 where the processor monitors user initiated service requests. If a user initiated service request is not detected at operation 1211, the data thread continues to completion at operation 1215. At operation 1216, the WCU 220 display is updated and the method continues at operation 1206 with the next periodic service request.

Thus, a system for the remote control of devices for endoscopy has been described. It should be appreciated that references throughout this specification to "one embodiment" or "an embodiment" means that a particular feature, structure or characteristic described in connection with the embodiment is included in at least one embodiment of the present invention. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the invention. In addition, while the invention has been described in terms of several embodiments, those skilled in the art will recognize that the invention is not limited to the embodiments described. The embodiments of the invention can be practiced with modification and alteration within the scope of the appended claims. The specification and the drawings are thus to be regarded as illustrative instead of limiting on the invention.

What is claimed is:

1. A method comprising:
  synchronizing a graphical user interface in a wireless control unit with a configuration of controllable endoscopic devices connected to a base unit of an endoscopic control system, wherein synchronizing the graphical user interface comprises:
    downloading files for a graphical user interface corresponding to the base unit;
    detecting a first configuration of controllable endoscopic devices connected to the base unit; and
    displaying a first set of icons in the graphical user interface corresponding to the first configuration of controllable endoscopic devices;
    detecting changes in the configuration of the controllable endoscopic devices; and
    automatically updating the graphical user interface in the wireless control unit with updated configuration information of the controllable endoscopic devices.

2. The method of claim 1, further comprising:
  selecting an icon for one controllable device of the first configuration of controllable endoscopic devices;
  requesting device status information from the base unit; and
  displaying controls and device status for the one controllable device corresponding to the selected icon.

3. The method of claim 2, further comprising:
  selecting a control for the one controllable device; and
  controlling the one controllable device with the wireless control unit.

4. The method of claim 1, wherein the first configuration of controllable endoscopic devices is changed to a second configuration of controllable endoscopic devices, wherein automatically updating the graphical user interface comprises:
  detecting the second configuration of controllable endoscopic devices; and
  displaying a second set of icons in the graphical user interface corresponding to the second configuration of controllable endoscopic devices.

5. The method of claim 4, further comprising:
  selecting an icon for one controllable device of the second configuration of controllable endoscopic devices;
  requesting device status information from the base unit; and
  displaying controls and device status in the graphical user interface for the one controllable device corresponding to the selected icon.

6. The method of claim 5, further comprising:
  selecting a control for the one controllable device; and
  controlling the one controllable device with the wireless control unit.

7. The method of claim 1, wherein the wireless control unit is one of a wireless Ethernet control unit, a Bluetooth control unit and a Blackberry control unit.

8. The method of claim 1, wherein the base unit and the controllable endoscopic devices comprise an endoscopic surgery suite.

9. A wireless control unit comprising:
  a processor;
  a user interface, coupled with the processor, comprising a display device; and
  a wireless network adaptor coupled with the processor, to communicate with a base unit of an endoscopic control system, wherein the processor is configured to:
    synchronize a graphical user interface on the display device with a configuration of controllable endoscopic devices connected to the base unit, wherein to synchronize the graphical user interface, the processor is configured to:
      download files for a graphical user interface corresponding to the base unit;
      detect a first configuration of controllable endoscopic devices connected to the base unit; and
      display a first set of icons in the display device for the first configuration of controllable endoscopic devices;
    receive changes in the configuration of controllable endoscopic devices from the base unit; and automatically update the graphical user interface in the wireless control unit with updated configuration information of the controllable endoscopic devices.

10. The wireless control unit of claim 9, wherein in response to a user's selection of an icon for one controllable device of the first configuration of controllable endoscopic devices, the processor is configured to:
request device status information from the base unit; and
display controls and device status for the one controllable device corresponding to the selected icon.

11. The wireless control unit of claim 10, wherein in response to a user's selection of a control for the one controllable device, the processor is further configured to control the one controllable device.

12. The remote control unit of claim 9, wherein the first configuration of controllable endoscopic devices is changed to a second configuration of controllable endoscopic devices, and wherein to automatically update the graphical user interface, the processor is configured to:
detect the second configuration of controllable endoscopic devices; and
display a second set of icons in the display device corresponding to the second configuration of controllable endoscopic devices.

13. The wireless control unit of claim 12, wherein in response to a user's selection of an icon for one controllable device of the second configuration of controllable devices, the processor is configured to:
request device status information from the base unit; and
display controls and device status for the one controllable device corresponding to the selected icon.

14. The wireless control unit of claim 13, wherein in response to a user's selection of a control for the one controllable device, the processor is configured to control the one controllable device.

15. The wireless control unit of claim 9, wherein the wireless network adaptor is one of a wireless Ethernet adaptor, a Bluetooth adaptor and a Blackberry adaptor.

16. The remote control unit of claim 9, wherein the base unit and the controllable endoscopic devices comprise an endoscopic surgery suite.

17. A base unit of an endoscopic control system for controlling devices during an endoscopic medical procedure comprising:
a system processor coupled to one or more controllable endoscopic devices; and
a wireless network interface configured to communicate with a wireless control unit, wherein the system processor is configured to:
detect a first configuration of the one or more controllable endoscopic devices;
synchronize a graphical user interface in the wireless control unit with the first configuration of the one or more controllable endoscopic devices connected to the base unit, wherein to synchronize the graphical user interface with the first configuration of the one or more controllable endoscopic devices, the system processor is configured to download files to the wireless control unit for a graphical user interface corresponding to the base unit, wherein the wireless control unit is configured to display a first set of icons corresponding to the first configuration of controllable endoscopic devices; and
automatically update the graphical user interface in response to changes in the configuration of the one or more controllable endoscopic devices.

18. The base unit of claim 17, wherein to automatically update the graphical user interface in the wireless control unit, the system processor is configured to:
detect a change in the configuration of the one or more controllable endoscopic devices from the first configuration to a second configuration; and
notify the wireless control unit of the change from the first configuration to the second configuration, wherein the wireless control unit is configured to display a second set of icons corresponding to the second configuration.

19. The base unit of claim 17, wherein the system processor is configured to receive commands from the wireless control unit to control one of the one or more controllable endoscopic devices in the first configuration.

20. The base unit of claim 18, wherein the processor is configured to receive commands from the wireless control unit to control one of the one or more controllable endoscopic devices in the second configuration.

21. An article of manufacture, comprising a machine-readable storage medium including data that, when read by a machine, cause the machine to perform operations, comprising:
synchronizing a graphical user interface in a wireless control unit with a configuration of controllable endoscopic devices connected to a base unit of an endoscopic control system, wherein synchronizing the graphical user interface comprises:
downloading files to the wireless control unit for a graphical user interface corresponding to the base unit;
detecting a first configuration of controllable endoscopic devices connected to the base unit; and
displaying a first set of icons in the graphical user interface corresponding to the first configuration of controllable endoscopic devices;
detecting changes in the configuration of the controllable endoscopic devices; and
automatically updating the graphical user interface in the wireless control unit with updated configuration information.

22. The article of manufacture of claim 21, wherein the first configuration of controllable endoscopic devices is changed to a second configuration of controllable endoscopic devices, wherein automatically updating the graphical user interface comprises:
detecting the second configuration of controllable endoscopic devices; and
displaying a second set of icons in the graphical user interface corresponding to the second configuration of controllable endoscopic devices.

* * * * *